United States Patent
Liang

(10) Patent No.: US 6,800,064 B2
(45) Date of Patent: Oct. 5, 2004

(54) DISINFECTING METHOD FOR WOUND WITHOUT USING LIQUID DISINFECTANT AND THE DEVICE THEREOF

(76) Inventor: Che-Peng Liang, No. 12-27, Lane 2, Chen Tung Rd., Feng Shan City, Kaohsiung Hsien (TW)

( * ) Notice: Subject to any disclaimer, the term of this patent is extended or adjusted under 35 U.S.C. 154(b) by 217 days.

(21) Appl. No.: 10/050,126

(22) Filed: Jan. 18, 2002

(65) Prior Publication Data

US 2003/0139734 A1 Jul. 24, 2003

(51) Int. Cl.$^7$ .......................... A61M 37/00; A61L 2/00; B01J 19/12
(52) U.S. Cl. .................. 604/25; 422/22; 422/186.07
(58) Field of Search .................. 128/202.25, 202.12; 604/23–25; 424/43–45; 607/94, 88; 422/186.07, 22–24, 186.12; 204/176

(56) References Cited

U.S. PATENT DOCUMENTS

| 5,052,382 A | * | 10/1991 | Wainwright | ........... 128/202.25 |
| 5,179,943 A | * | 1/1993 | Hama et al. | ................. 607/107 |
| 6,060,020 A | * | 5/2000 | Piuk et al. | ..................... 422/33 |
| 6,110,431 A | * | 8/2000 | Dunder | .................. 422/186.12 |
| 6,283,986 B1 | * | 9/2001 | Johnson | ....................... 607/94 |
| 6,426,053 B1 | * | 7/2002 | Barnes | ..................... 422/186.3 |
| 6,576,190 B1 | * | 6/2003 | Park | ............................ 422/28 |

FOREIGN PATENT DOCUMENTS

| JP | 01160805 A | * | 6/1989 |
| SE | SU 853833 B | * | 8/1981 |

* cited by examiner

Primary Examiner—John J. Calvert
Assistant Examiner—Linh Truong
(74) Attorney, Agent, or Firm—Rosenberg, Klein & Lee

(57) ABSTRACT

A wound disinfecting device without using liquid disinfectant includes a main body, a control unit, a fan, an ozone generating unit, an ultraviolet generating unit, and an anion generating unit, which are all received in the main body. The main body has a front air outlet, and a rear air inlet. The fan is disposed adjacent to the rear air inlet. When the device is activated, ozone generated by the ozone unit is blown to outside by means of the fan such that a wound can be disinfected by the ozone, ultraviolet rays generated by the ultraviolet ray generating unit, and anions generated by the anion generating unit when the front air outlet is held close to a wound without coming into contact therewith.

3 Claims, 4 Drawing Sheets

DISINFECTING METHOD FOR WOUND WITHOUT USING LIQUID DISINFECTANT AND THE DEVICE THEREOF

BACKGROUND OF THE INVENTION

The present invention relates to a wound disinfecting method without using liquid disinfectant, and more particularly a would disinfecting method wherein ozone of high concentration, ultraviolet ray, and anions are applied to the wound for destroying the bacteria. Conventionally, cotton wool or cotton buds with liquid disinfectant such as iodine solution are used to destroy the bacteria on a wound; the cotton wool or cotton buds are rubbed or pressed against the wound such that the liquid disinfectant can be applied over the same, This method is found to have disadvantages as follows:

1. The rubbing of the cotton wool against the patient's wound will make the patient feel a great deal of pain.

2. The liquid disinfectant will soften the scar, and the rubbing of the cotton wool against the scar is likely to tear the scar open.

3. If the cotton wool with liquid disinfectant is left on the wound for providing sufficient disinfectant on the wound, the cotton wool would stick to the wound when it becomes dry. Consequently, the patient is likely to feel a great deal of pain, and the wound might be torn open when the cotton wool is removed from the wound.

4. The rubbing of the cotton wool against the wound is likely to cause the stitch to become loose that fastens the edge of the wound, causing the skin to have an unpleasant-looking opening.

SUMMARY OF THE INVENTION

Therefore, it is main object of the present invention to provide a wound disinfecting method wherein the wound is disinfected by ozone blowing onto the wound from an ozone generating unit, which doesn't come into contact with the wound; thus, eliminating the disadvantages of the conventional method.

The wound disinfecting method without using liquid disinfectant according to the present invention uses ozone, ultraviolet rays as well as anions such that the disinfecting effect thereof is enhanced. A wound disinfecting device used in the present method includes a main body, a control unit, a main fan, an ozone generating unit an ultraviolet generating unit and anion generating unit, which are all disposed in the main body. The main body has a front end air outlet, and a rear end air inlet. When the device is activated, ozone, ultraviolet rays, and anions are generated by the above-mentioned generating units such that when the air outlet is held close to a wound, the wound can be disinfected by the ultraviolet rays, the anions and the ozone, which is blown out through the air outlet by means of the fan.

BRIEF DESCRIPTION OF THE DRAWINGS

The present invention will be better understood by reference to the accompanying drawings, wherein.

DETAILED DESCRIPTION OF THE PREFERRED EMBODIMENT

Figure 1:
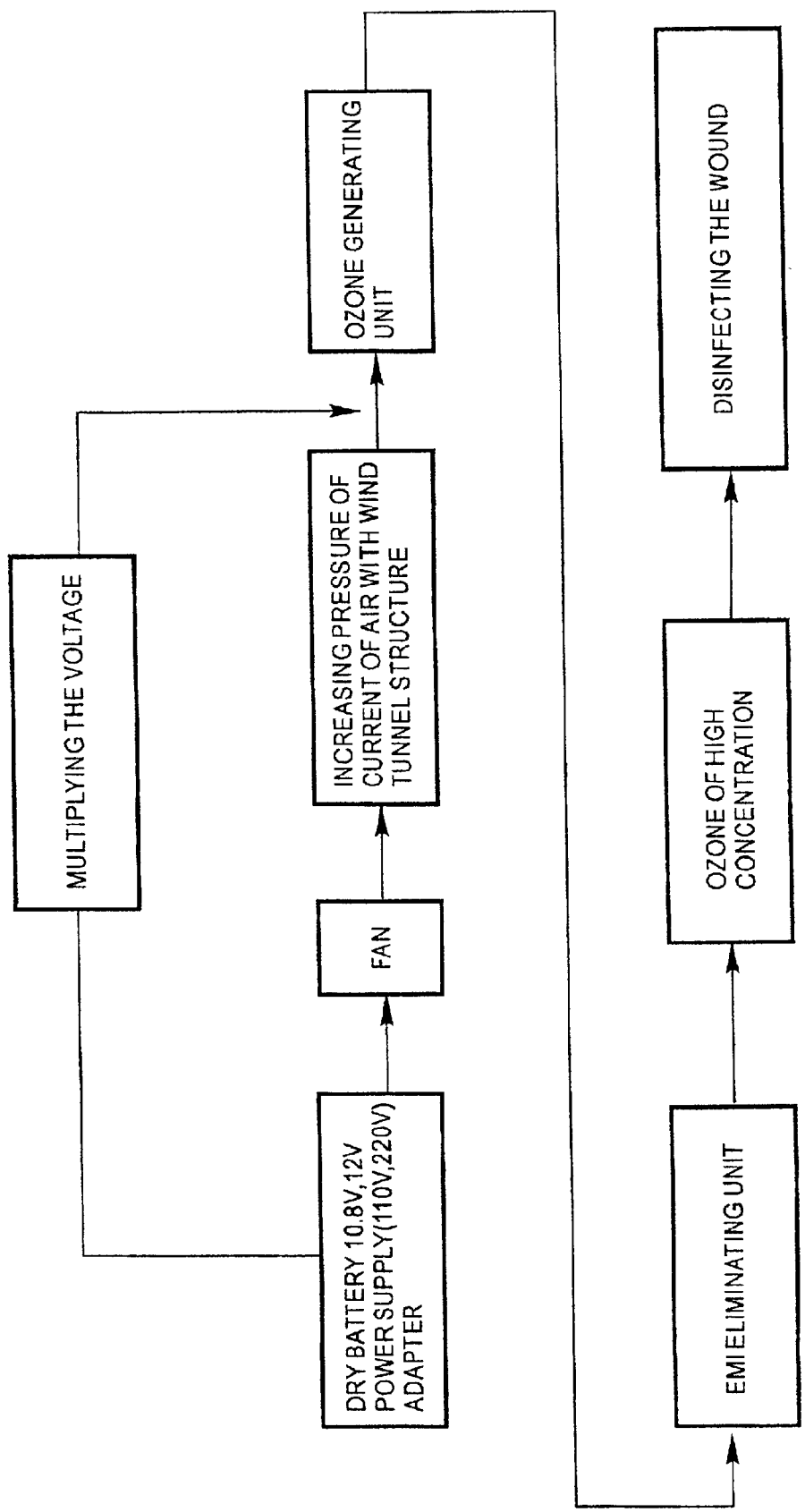
FIG. 1 is a flow chart of the wound disinfecting method of the present invention.

Referring to FIG. 1, a wound disinfecting method according to the present invention includes the following steps:

(1) supplying the power to a whole system of the present method; the power can be 10.8 or 12 voltage dry battery, or 110 or 220 voltage alternating current; a power converter can be used together with a switch 13 (referring to FIG. 2) to supply suitable power;

(2) supplying current of air of increased pressure with a main fan 3 (FIG. 2) and a wind tunnel structure; the main fan 3 is preferably a turbine fan so as to be able to increase the pressure of the current of air together with the wind tunnel structure;

(3) multiplying the voltage; the voltage is multiplied to such a degree that electric discharge can happen in a condition similar to that of lightning; an ozone generating unit is also used to generate ozone of high concentration;

(4) eliminating electromagnetic interference (EMI) such that the interference of static electricity of electromagnetic waves can be substantially eliminated;

(5) blowing out the ozone to the wound by means of the turbine fan and other auxiliary fans;

(6) disinfecting the wound; passing the ozone over the wound for destroying the bacteria therein and therearound.

Thus, the wound can be disinfected without using liquid disinfectant or coming into contact with the ozone generating unit.

In addition, ultraviolet rays of suitable strength that can't cause damage to human body are generated by an ultraviolet ray generating unit 5 in step (3) such that the wound can be disinfected by means of both ozone and ultraviolet rays; high voltage anions are generated by a anion generating unit 6 for disinfecting and making the cells in wound become more lively. A special isolation treatment should be done on the whole system of the present wound disinfecting method for preventing the ultraviolet from causing damage to the health of the person using the present device.

Figure 2:
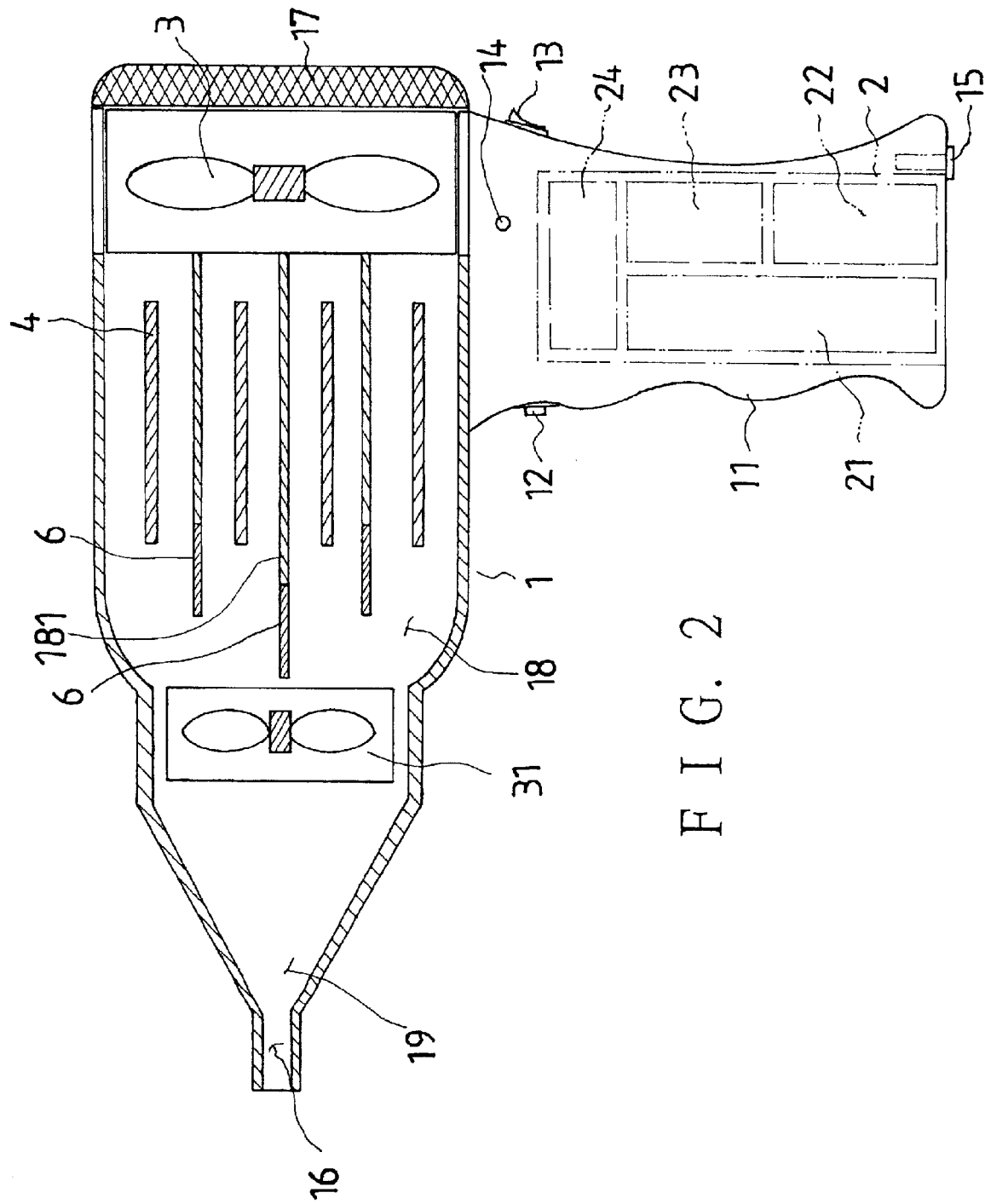
FIG. 2 is a cross-sectional view of the wound disinfecting device of the present invention.
Figure 3:
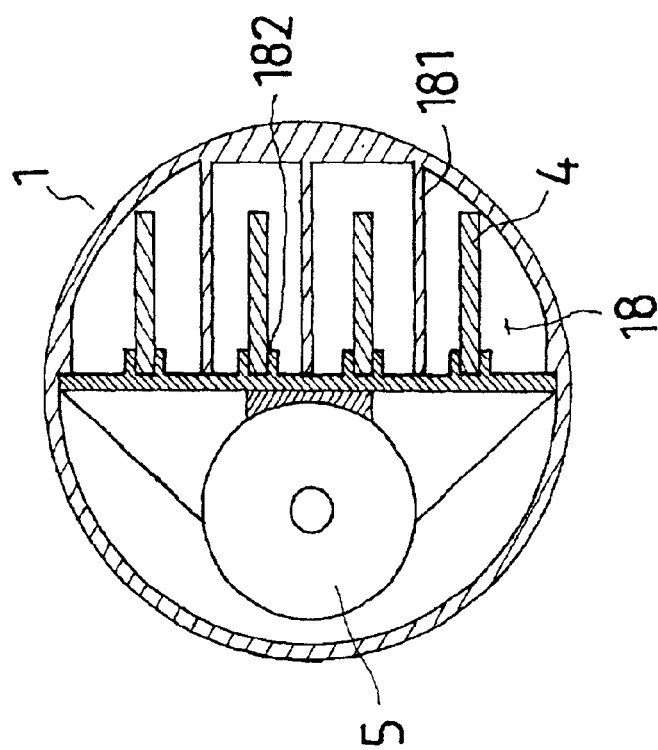
FIG. 3 is a front view of the main body of the wound disinfecting device of the present invention.
Figure 4:
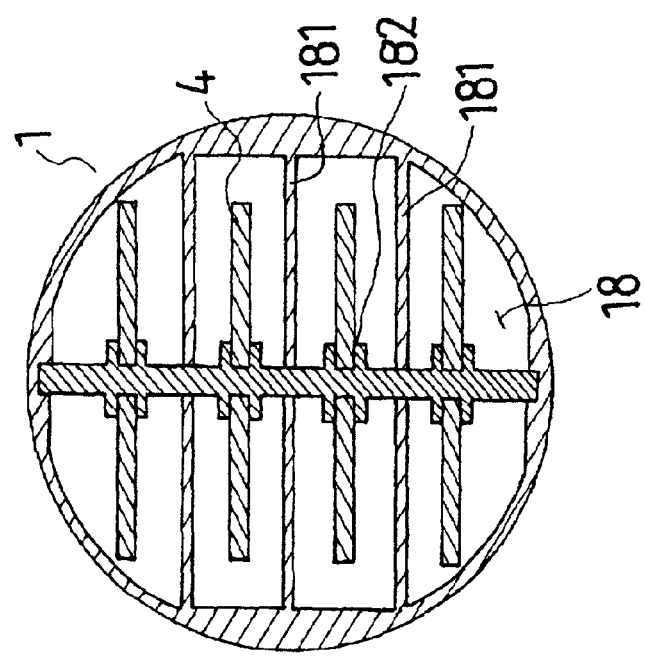
FIG. 4 is a rear view of the main body of the wound disinfecting device of the present invention.
Figure 5:
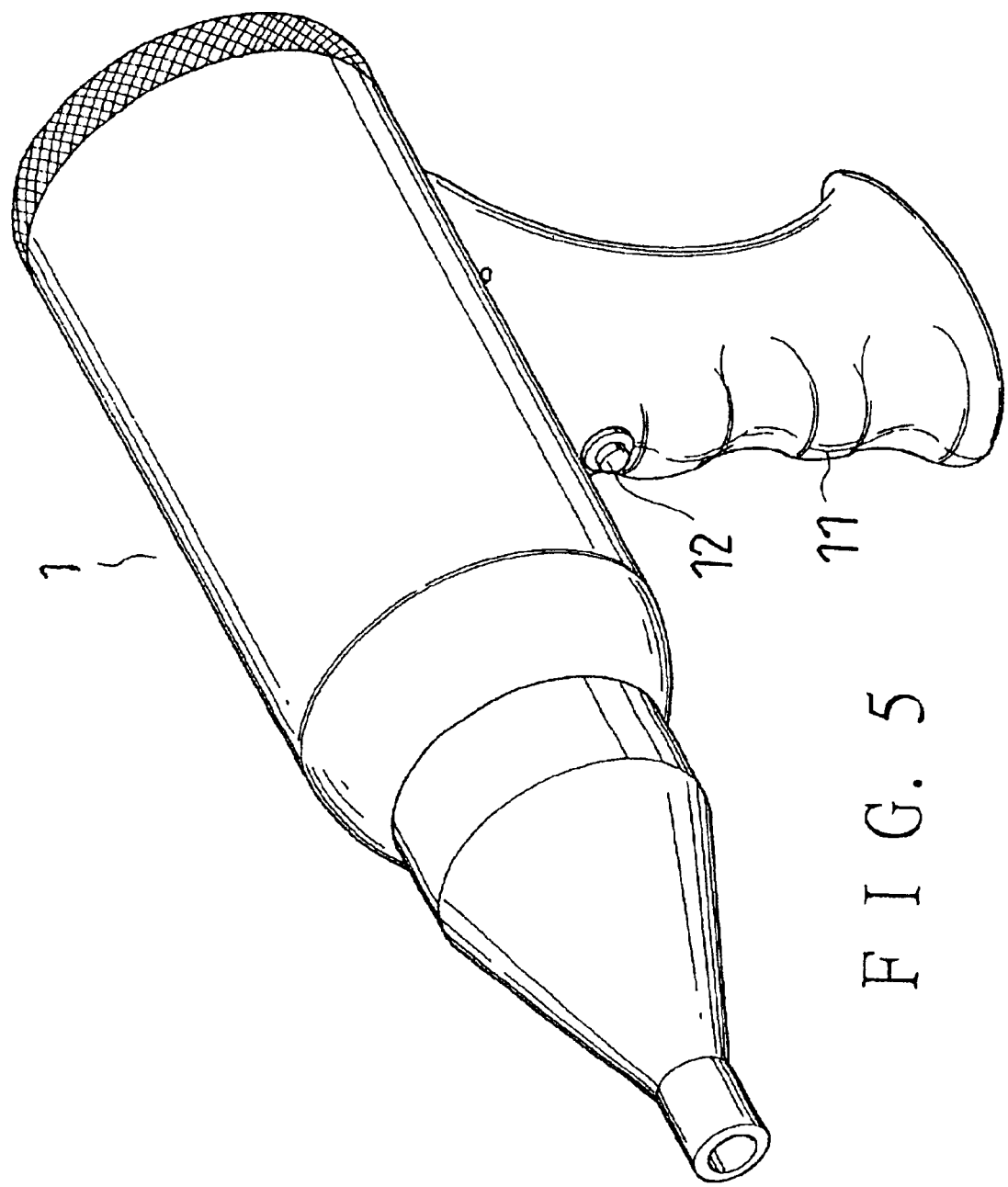
FIG. 5 is a perspective view of the wound disinfecting device of the present invention.

Referring to FIGS. 2, 3 and 4, a device used in the wound disinfecting method of the present invention includes a main body 1, a control unit 2, a main fan 3, ozone generating units 4, an ultraviolet ray generating unit 5, and an anion generating unit 6.

The main body 1 has a handle 11 at the rear lower part, a receiving room 18, an air inlet 17 at the rear end, an air outlet 16 at the front end; a front portion 19 of the main body 1 tapers off towards the front end. The handle 11 receives the control unit 2, which includes a dry battery 21, a selection circuit 22, a voltage multiplying and rectifying circuit 23, and an electromagnetic interference (EMI) eliminating circuit 24. An on/off switch 12, a power terminal 15, a selection switch 13 and an indicating lamp 14 are fitted to the outer side of the handle 11, and electrically connected to the control unit 2.

A filter net can be fitted onto the air inlet 17 with plant extracted essence being applied thereover. The main fan 3 is disposed at the rear portion of the main body 1. Several compartment boards 181, and fixing elements that have holding trenches 182, are disposed in the receiving room 18;

the anion generating unit 6 is disposed at the front end of the compartment boards 181, while the ozone generating units 4 are fitted to the holding trenches 182 of the fixing elements. The power terminal 15 is provided for connection to a power cord.

Referring to FIG. 2 again, an auxiliary fan 31 is disposed between the tapering front portion 19 and the ozone generating units 4. In addition, an ultraviolet ray generating unit 5 is disposed near the ozone generating units 4; a special isolation treatment is done over the main body 1 for preventing the ultraviolet rays from causing damage to the health of the user.

In using the wound disinfecting device, the selection switch 13 is pushed to a proper position according to the type of power that is being used. Then, the on/off switch 12 is pushed for activating ozone generating units 4, the main fan 3, the ultraviolet generating unit 5, the anion generating unit 6 and the auxiliary fan 31. Because the voltage multiplying and rectifying circuit 23 will multiply the voltage, electric discharge can happen on the ozone generating units 4 for allowing same to generate ozone of the high concentration. And the EMI eliminating circuit 24 will reduce the interference of static electricity of electromagnetic waves such that the ozone gas of high concentration can be provided with relatively low C. In addition, the ultraviolet ray generating unit 5 will generate ultraviolet rays of suitable strength that can't cause damage to human body, and the anion generating unit 6 will generate anions of relatively high voltage to help the ozone destroy the bacteria on the wound and the cells of the wound to be come more lively, helping the wound heal up more quickly.

From the above description, it can be easily understood that the wound disinfecting device of the present invention has the following desirable features:

1. The user doesn't have to rub the front end air outlet of the device against the wound eliminating the risk of making the patient feel a great deal of pain.
2. Because the device doesn't come into contact with the wound when the disinfecting ozone is applied on the wound, there is no rubbing force like the conventional method that would interfere with the healing up of the wound.
3. The disinfecting effect of the present device can be further enhanced with the ultraviolet rays and the anions. And, the cells of the wound can become move lively because of the ozone and the anions.
4. The wind blowing from the fans for moving the ozone can also help relieve the pain of the patient.
5. The present wound disinfecting device is relatively compact and easy to use; no matter what body part the wound is on, the disinfection can be performed with ease.
6. The present disinfecting method can reduce the risk of the wound getting infected because the device doesn't come into contact with the wound. Therefore, the wound can heal up relatively rapidly, and the medical staff can be protected from infection too.
7. There won't be any medical waste left after the disinfection, i.e. the present method is better than the conventional one from the viewpoint of environmental protection.
8. The wound disinfecting device is small in size so it can be carried easily.

What is claimed is:

1. A wound disinfecting method, comprising the steps of:
   (a) establishing a power source for providing electrical power for a turbine fan, a wind tunnel and an ozone generatng unit;
   (b) supplying a current of air; a pressure of said current of air being increased with said turbine fan and said wind tunnel;
   (c) multiplying a voltage of said electrical power, the voltage being multiplied to such a degree that an electric is generated, said ozone generating unit generating ozone of high concentration;
   (d) eliminating electromagnetic interference so as to eliminate interference of static electricity of electromagnetic waves;
   (e) blowing the ozone of step (c) out by means of said turbine fan and other auxiliary fans; and,
   (f) disinfecting a wound; the ozone being passed over the wound for destroying bacteria therein and therearound.

2. The wound disinfecting method as claimed in claim 1, wherein step (c) further includes supplying ultraviolet rays by means of an ultraviolet ray generating unit for disinfecting the wound; an isolation treatment being done on said whole system for protecting a user from said ultraviolet rays.

3. The wound disinfecting method as claimed in claim 1, wherein step (c) further includes supplying anions by means of an anion generating unit for disinfecting the wound.

* * * * *